United States Patent [19]
Lappe

[11] Patent Number: 5,929,422
[45] Date of Patent: Jul. 27, 1999

[54] ON-SITE MACHINE READABLE ASSAYING SYSTEM

[75] Inventor: Murray Lappe, Beverly Hills, Calif.

[73] Assignee: National Medical Review Office Inc., Los Angeles, Calif.

[21] Appl. No.: 08/832,957

[22] Filed: Apr. 4, 1997

[51] Int. Cl.$^6$ .............................. G06F 7/10; G01N 33/00
[52] U.S. Cl. .............................. 235/462.13; 235/462.01; 235/462.04; 422/56
[58] Field of Search .................................... 235/462, 375, 235/499, 462.04, 462.13, 462.01; 422/56, 66

[56] References Cited

U.S. PATENT DOCUMENTS 4,042,329  8/1977  Hochstrasser .............................. 422/58
4,059,407  11/1977  Hochstrasser .............................. 422/56

*Primary Examiner*—Donald Hajec
*Assistant Examiner*—Drew A. Dunn
*Attorney, Agent, or Firm*—Goldstein & Canino

[57] ABSTRACT

A machine readable assaying system comprising a test card having machine readable assaying means. A plurality of individual analysis strips, each strip comprising antibodies and/or reagents capable of indicating the positive presence of distinct illicit substances form a pattern of elements including one or more fixed strips and one or more blank regions. The detection of the presence of a particular substance or drug will result in one or more of the analysis strips changing from a first (light reflective) color to a second darker (light absorbent) color. The pattern of analysis strips, fixed strips and blank regions may be provided to encode one or more characters/digits of information. By the inclusion of the analysis strips with the plurality of fixed strips and blank regions, the detection of one or more illicit substances may alter the overall pattern of fixed and test strips and blank regions, and hence cause the encoded information represented thereby to be altered. Accordingly, the particular pattern of bars and spaces that result from an exposure the physiological fluids of a donor is contemplated to produce a distinct machine readable indicia. The transformation which occurs on the test card will be uninterpretable by the administrator of the test, thus preserving the anonymity and privacy of the tested individual.

13 Claims, 4 Drawing Sheets

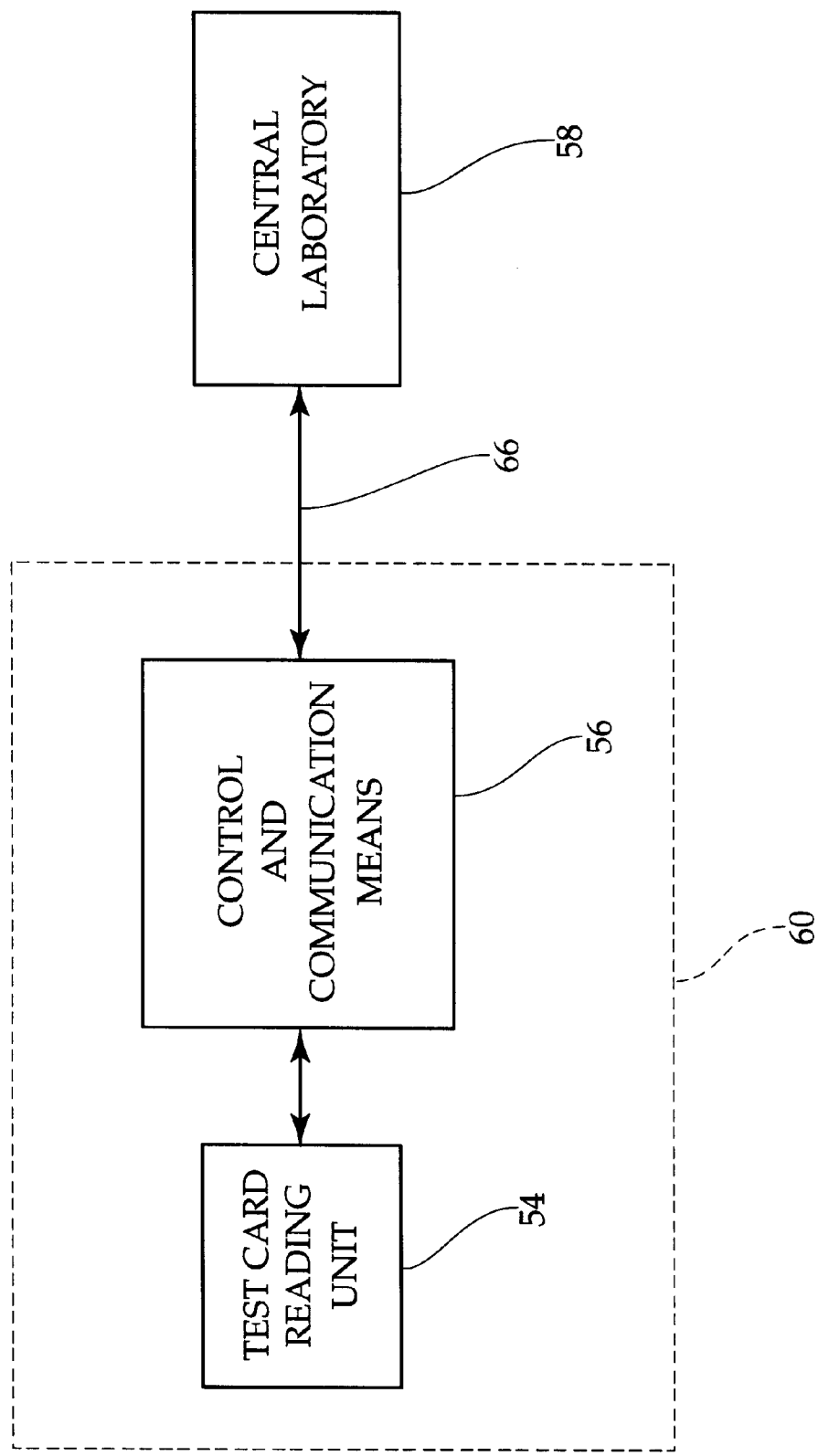

ON-SITE MACHINE READABLE ASSAYING SYSTEM

BACKGROUND OF THE INVENTION

The invention relates to an assaying system. More particularly, the invention relates to a machine readable assaying system for analyzing a specimen of physiological fluid to detect the presence or absence of particular substances therein. In a preferred embodiment, the machine readable assaying system contemplates the utilization of machine readable bar-code patterns imprinted upon a test card which change form in response to a physical, chemical or biological reaction. The test result which is encoded within the bar-code indicia imprinted upon the test card is read by an appropriate decoding apparatus (i.e. a bar-code reader/scanner), and the decoded results are stored in a memory unit and transmitted, if desired, to a distinct location. A test administrator merely scans the bar-code. Because the bar-code patterns change form in such a subtle yet varied manner, the administrator or another observer of the test card is unable to discern the results. Accordingly, the privacy interests of the donor are preserved, as well as human interpretation errors, transcription and translation errors.

The increase in drug use over the past several decades has created a sharp need for more effective, expeditious methods of analyzing whether a particular individual is a user of certain illegal substances. Both private industry employers as well as governmental employers often need to determine whether an individual has drug residue present in his or her biological system, and hence determine whether such an individual is a drug user or drug abuser and thus an unqualified employee.

Typically, the status of an individual as a drug user or abuser is determined by analysis of the individual's physiological fluids, namely urine. A specimen of urine is collected, and a highly sensitive screening test is first performed, usually at a centralized laboratory. If specimen samples screen positive at the central laboratory, then a more sensitive and controlled confirmation analysis must be performed.

In addition to being an extremely costly process, the above mentioned procedure also involves great time delays to employers desirous of obtaining new qualified employees. Upon collection of the urine sample, the employer must wait to receive test results from the central laboratory before hiring any potential employees. Furthermore, the massive amount of handling and transfer of the sample of urine from the initial collection site to the central laboratory.

To combat the above mentioned timeliness problem which faces many employers in awaiting results from the central laboratory, various "on-site" or "hand-held" assaying devices have been developed. A major problem inherent in these "on-site" testing devices is that the privacy concerns of the potential employee being tested are not adequately addressed. Since all of the on-site testing devices available heretofore attempt merely to identify drugs present (i.e. simply to indicate which specimens do indeed possess the prohibited substance/drug), the anonymity of a presumptive positive donor is impossible to conceal. Due to such lack of anonymity, many employers (governmental in particular) will not employ such an assaying system as it does not comply with federally mandated regulations regarding privacy and civil liberties during drug-employment testing. A more anonymous, reliable and expeditious assaying system is needed, wherein negative results can be obtained quickly without compromising the privacy concerns of the tested individual. The results are not "human readable" and thus are not subject to interpretation.

SUMMARY OF THE INVENTION

It is an object of the invention to produce an assaying system for analyzing a specimen of body fluid to detect the absence of particular substances therein.

It is another object of the invention to provide an assaying system which provides more anonymous, reliable and expeditious results than those assaying systems presently found in the art, wherein said results can be obtained quickly without compromising the privacy concerns of the tested donor individual.

It is a further object of the invention to provide an on-site, portable assaying system which allows the results of said assay to be determined and utilized almost immediately by an employer, without jeopardizing the privacy rights of the individual being tested.

It is a still further object of the invention to provide an assaying system which allows the results of said assay to be encoded in a machine readable format (such as bar-coding) such that said encoded results are visually undetectable and must be de-coded by appropriate apparatus. Accordingly, the administrator of the assay lacks access to the test results.

It is yet another object of the invention to provide an assaying system which possesses a memory unit to store resultant decoded assay data, and communication means for transmitting said decoded data to a distinct location (such as a central laboratory/processing office). Upon receiving the assay data, the central laboratory/processing office could then electronically, telephonically or manually (via a delivered hard copy) communicate a responsive "negative test certificate" to the employer for those individuals testing negative (indicating that these individuals are candidates for immediate employment). A sample specimen of physiological fluid from only those individuals who tested positive would then be requested by the central laboratory for standard "confirmation" testing.

It is yet another object of the invention to provide an assaying system such as that discussed above which possesses means capable of detecting adulteration of the specimen.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

FIG. 2 is a high level functional diagram of an embodiment of an assaying system apparatus to read/interpret the test card of FIG. 1A in accordance with the invention.

DETAILED DESCRIPTION OF THE PREFERRED EMBODIMENTS

FIG. 1 depicts a test card 22 of an on-site machine readable assaying system, having various indicia inscribed thereupon. More specifically, the test card 22 possesses machine readable assaying means 32 (also to be referred to hereafter as an encoded machine readable data source). The machine readable assaying means 32 preferably comprise in part a plurality of individual analysis strips 34, each consisting of antibodies and/or reagents capable of chemically analyzing a sample volume of urine to detect a positive presence of a particular substance (such as marijuana, opiates, amphetamines, cocaine, PCP, etc.). Traditionally, assaying means in this particular field were configured merely to visually indicate the positive presence of particular substances. If a "positive" indication was given, it was automatically inferred that the donor individual who provided the urine was a drug user/abuser (although secondary testing is always conducted to confirm these results). This system posed great threats to individual privacy and civil liberty concerns, and hence proved unsatisfactory. The employment of the assaying means by the instant invention, however, addresses these deficiencies.

Figure 1A:
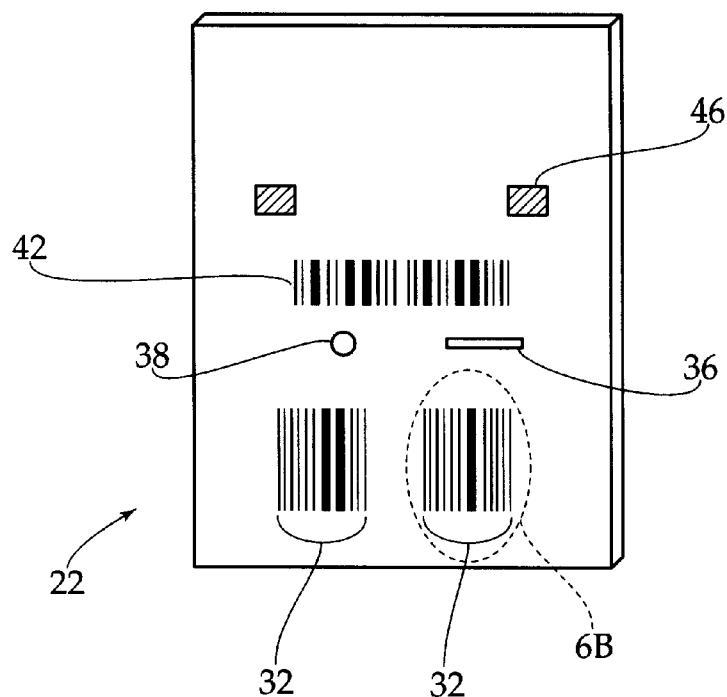
FIG. 1A illustrates a diagrammatic perspective view of a test card of an on-site machine reable assaying system.
Figure 1B:
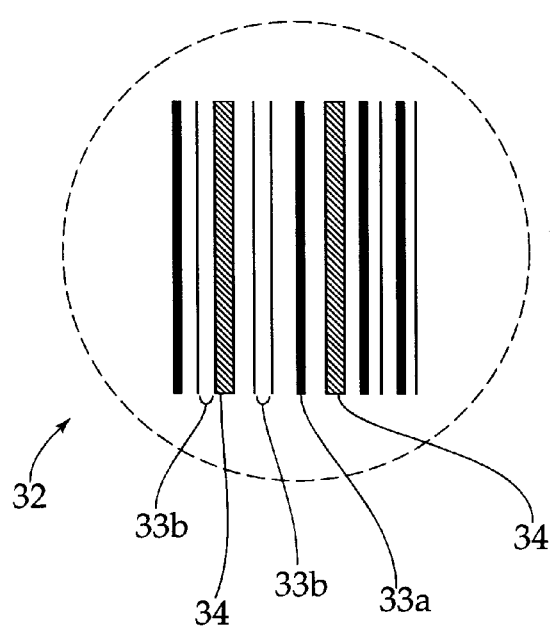
FIG. 1B illustrates an enlarged portion of the embodiment of the test card of FIG. 1A.

As seen in detail in FIG. 1B, the plurality of individual analysis strips 34 are illustrated as an essential component of the machine readable assaying means 32 (also referred to as bar code indicia). As mentioned earlier, each of said analysis strips 34 consists of the antibodies and/or reagents which are capable of visually indicating the positive presence of distinct illicit substances. In particular, the machine readable assaying means 32 may be formed, as shown in FIG. 1B, of a pattern of elements including one or more fixed strips 33a, one or more blank regions 33b, and the analysis strips 34, to produce the encoded machine readable data source. In a preferred embodiment, the detection of the presence of a particular substance or drug will result in one or more of the analysis strips 34 changing from a first (light reflective) color to a second darker (light absorbent) color—or visa versa.

As seen in the arrangement depicted in FIG. 1B, the pattern of analysis strips 34, fixed strips 33A, and blank regions 33B (which may also be termed "bars" and "spaces" by those skilled in the art), when configured to comprise the encoded machine readable data source may be provided to encode one or more characters/digits of information or other data. Accordingly, by the inclusion of the analysis strips 34 along with the plurality of fixed strips 33a and blank regions 33b, the detection of one or more illicit substances may cause the overall pattern of fixed 33A and test 34 strips (bars) and blank regions 33B (spaces) to vary, and hence the encoded information represented thereby to be altered. For example, machine readable assaying means 32 comprising the encoded machine readable data source may be comprised of one or more bar code indicia whose pattern of bars and spaces (and associated coded digits) is altered in accordance to the particular substances detected via the inclusion and appearance of one or more analysis strips 34 within the bar code indicia. Accordingly, the particular pattern of bars and spaces that result from an exposure the physiological fluids of a donor, as provided by the machine readable assaying means 32, is contemplated to produce a distinct machine readable indicia.

It is contemplated in the preferred embodiment that one or more of the individual analysis strips 34 which comprise the bar code indicia of the machine readable assaying means 32 contain reagents or antibodies whose visual appearance is altered in response to physiological fluid, regardless of whether any illicit drugs are present within said fluid. It is further contemplated that these "control" analysis strips 34C be situated such that their detection amongst the pattern of strips 33A and 34 and blank regions 33B (bars and spaces) comprising the bar code indicia does not vary the character of the information encoded therewithin. For instance, the bar code indicia of the machine readable assaying means 32 would indicate, if decoded by an appropriate device prior to contact with physiological fluid, a negative presence of illicit drugs. Upon contact with a volume of physiological fluid which lacks the presence of illicit drugs, the "control" analysis strips 34C will appear. However, their placement amongst the standard test strips 34, fixed test strips 33A and blank regions 33B will not effect the initial encoded character of the bar code indicia. Accordingly, a negative assay will be determined.

The function of the "control" analysis strips 34 is to prevent an administrator of the test from learning the outcome of the assay. If, subsequent to the administration of each assay, some type of change occurs to the visual appearance of the machine readable assaying means 32, then the test administrator will be unable to discern positive test results from negative results. Only the device used to decode the encoded bar code indicia will be able to determine whether the donor's specimen of physiological fluid tests positive for illicit drugs, and if so, which particular substances were present.

The test card 22 of FIG 1A also possesses adulteration detection means 36. Said adulteration detection means 36 are capable of determining whether a particular specimen of urine or other physiological fluid has been tampered with by administering either chemical analysis (to ensure that the chemical composition of said specimen is consistent with that of standard, non-adulterated human urine) and/or temperature analysis (to ensure that the specimen has been recently excreted from the donor and has not been brought to the test site by the donor from an earlier excretion). Furthermore, quality control indication means 38 are also present upon said test cards 22 to ensure that the reagents of the analysis strips 34 are functioning properly. Said quality control indication means 38 are configured to generate a signal upon contact with urine or other physiological fluids, regardless of the presence of illicit substances, to indicate that the analysis strips 34 have not been degraded due to improper storage, etc. If the quality control indication means 38 fail to generate a signal upon contact with the urine, the test card 22 should be discarded.

Further included upon the test card 22 of FIG 1A is an identification code 42, which may be provided as a pattern encoding items such as production batch numbers of the test card, a date of manufacture, etc. It is important to note that the identification code 42 pattern represents a machine readable (and decodeable) pattern, and as such may easily be "read" by a suitable device and received by a computer or controller means for processing, dissemination, or other appropriated actions.

Also seen in FIG 1A are alignment aids 46 that may be provided to aid in the alignment of the test card 22 for reading or scanning by a properly arranged device. It is important to note that other arrangements of the identification code 42, the quality control indication means 38, the adulteration means 36, and the assaying means 32 are possible and contemplated. For example, skilled persons will appreciate modifications such as including the quality control indication means 38 and the adulteration means 36 within the elements composing the assaying means 32, as seen in FIG. 1B. Accordingly, quality control indication means 38 and the adulteration means 36 may determine the overall "coding" provided by said assaying means 32. In one embodiment of the instant invention, it is contemplated that the quality control indication means 38 be incorporated with the "control" test strips 34 and situated such that their detection amongst the pattern of strips 33A and 34 and blanks 33B (bars and spaces) comprising the bar code indicia does not vary the character of the information encoded therewithin. Still other modifications are possible and contemplated.

Turning now to FIG. 2, there is provided a high level functional diagram of a test card reading apparatus 60. As shown, a test card reading unit 54 is included, which is operatively coupled to a control and communication means 56. The test card reading means 54 is provided to "read" and determine the particular patterns present on the test card 22. As such, the reading of the patterns of the test card 22 may result in a plurality of digits or characters being determined (or generated) by the test card reading units 54, which may be communicated to a control and communication means 56. Subsequently, the received characters may be transmitted, via a communication link 66, to a central laboratory 58 for checking, decoding, and or general evaluation. Therefore, the pattern of the assaying means 32, the condition of the adulteration detection means 36 and the quality control indication means 38, and the identification code may be provided as "machine readable" and may be transmitted in an anonymous and confidential manner to the central laboratory 58, in accordance with the privacy features of present invention. Those skilled in the art will appreciate the available means to embody the test card 22 of FIG. 1A, and further may provide modifications and alterations to the embodiments of the test card reading apparatus 60 of FIGS. 2 and 3.

Figure 3:
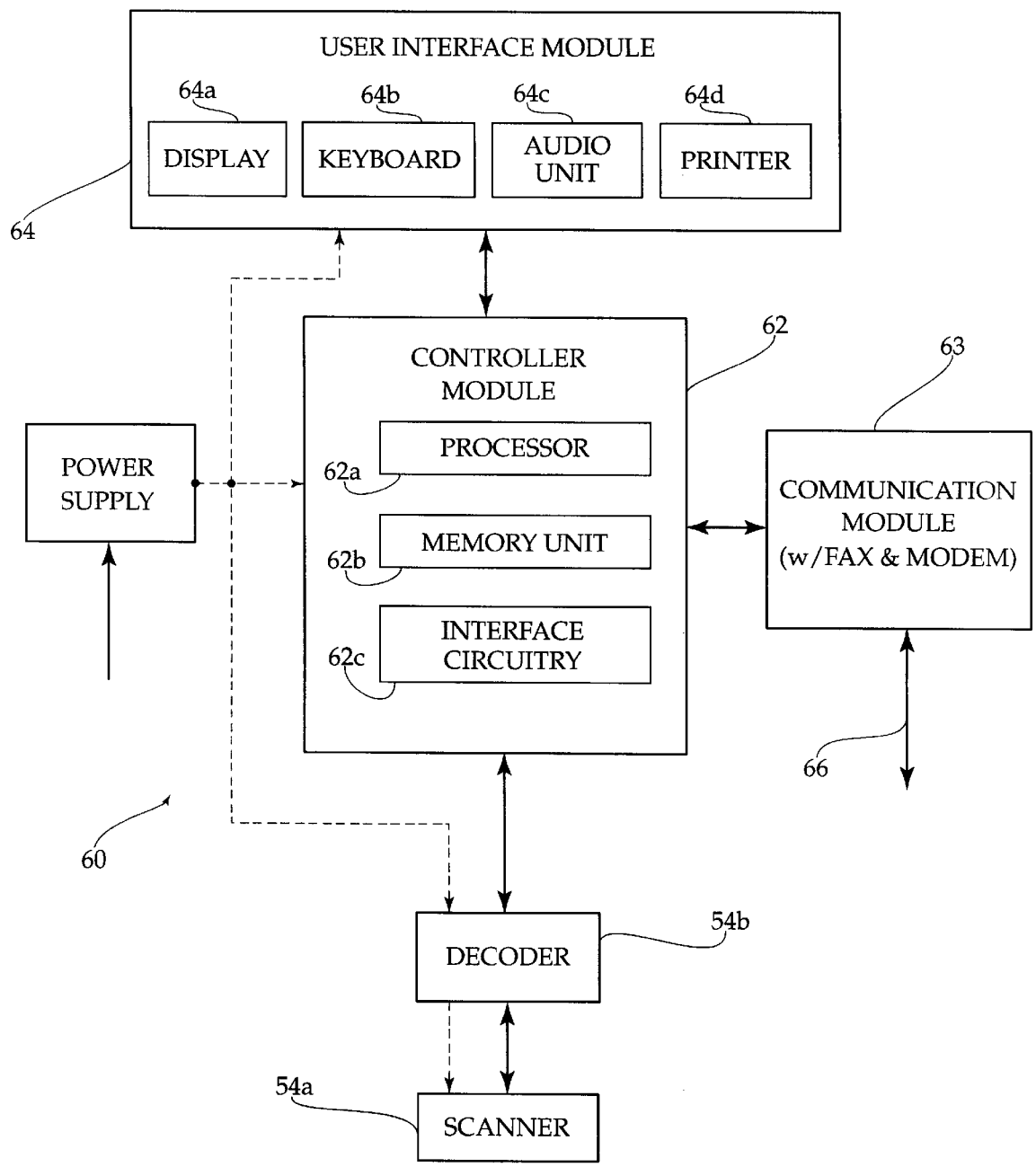
FIG. 3 provides a more detailed block diagram of an embodiment of if the apparatus of FIG. 2.

One possible embodiment of the test card reading apparatus 60 is seen in FIG. 3. Included is a scanner 54a and decoder 54b configured to read the test card 22 and decode the plurality of patterns contained thereon. The patterns may include the assaying means 32, the identification code 42, the adulteration detection means 36, and the quality control indication means 38. A controller module 62 is provided to establish the functional characteristics of the test card reading apparatus 60. The controller module 62 may be embodied as shown by providing a processor 62a, a memory unit 62b (providing a suitable application program), and any required interface circuitry 62c. The controller module may be arranged to receive from the decoder information including one or more (decoded) digits or characters. The information may then be transmitted by a communication module 63 via the communication link 66 to the central laboratory 58. The information processed and or transmitted to the central laboratory 58 for analysis. Also shown is a user interface module 64 to enable an individual to enter information into the test card reading apparatus 60 and provide information to said individual. The user interface may include known items such as a display 64a, a keyboard 64b, an audio unit 64c, and printer 64d. For example, an identification code such as the donor's social security number may be keyed into the keyboard 64B of the user interface module 64 and transmitted via the communication link 66 to the central laboratory 58. Other user interface items may also be provided (which are not shown in FIG. 3) including pointing devices, a fax transmission module, touch screen displays, etc.

It should be noted that the controller module 62 may be provided by known programmable single chip microcomputers and any additional analog/digital circuitry required. Further, it is contemplated that the controller module 62 may be provided (in an alternate embodiment to that shown in FIG. 3) by one or more programmable logic devices (PLDs), or by discrete components including digital MSI and LSI logic functions. Those skilled in the art will appreciate the plethora of commercially available (off-the-shelf) devices and components that may be utilized to embody the controller module 62 and the communication module 63. Also, although the scanner 54b may in a preferred embodiment be realized by a laser scanning device, other suitable devices, such as a CCD imaging device may be employed. It is also contemplated that the test card reading apparatus 60 may be realized by a properly configured personal or workstation computer. For example, an IBM® compatible personal computer (PC) may be arranged with a scanner 54a, a fax modem or networking card, etc. In such an embodiment, the functionality of the test card reading apparatus 60 may be provided by the execution of an (custom) application program. Therefore, it should be understood that the embodiments of the FIGS. 3 and 4 are illustrative of a number of possible embodiments, which may be provided by skilled persons.

Figure 4:
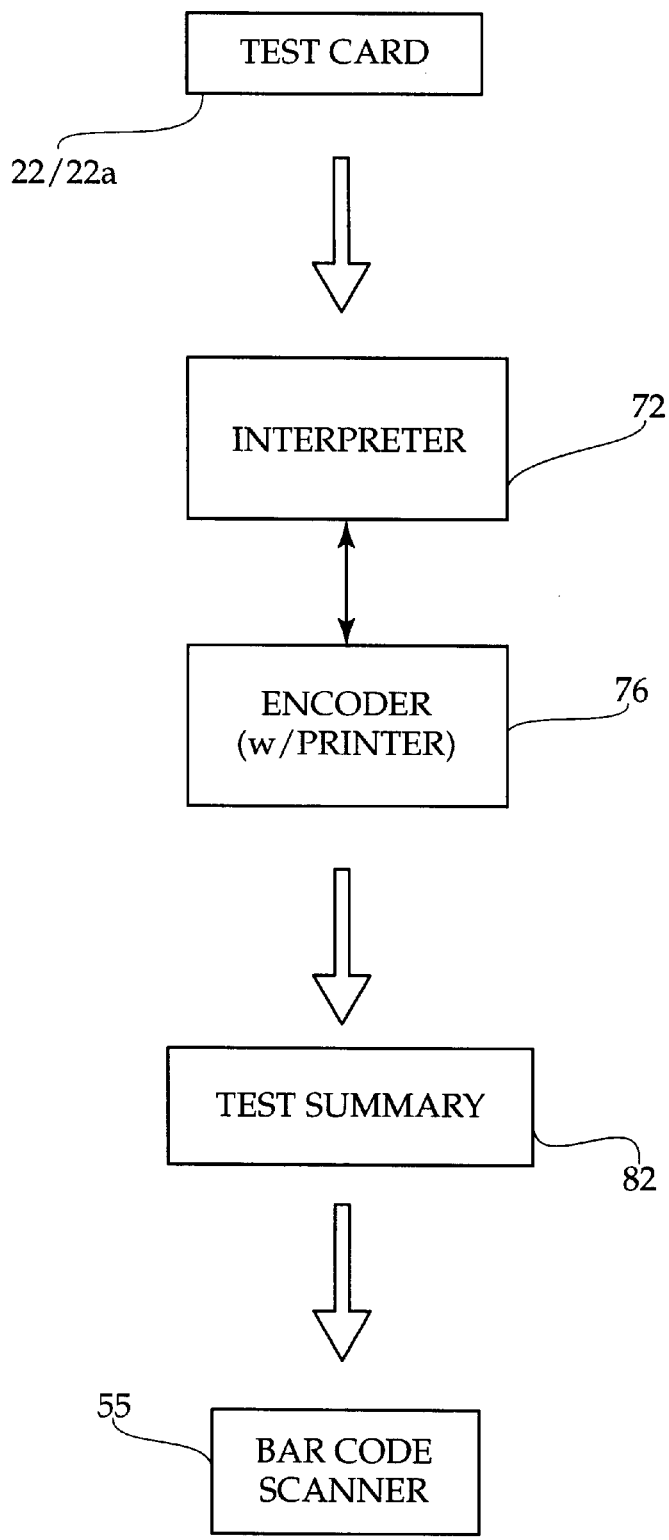
FIG. 4 provides another embodiment of an apparatus to read/interpret test cards of the present invention.

Another embodiment of the test card reading unit 54 of FIG. 2 is provided in FIG. 4. An important feature of this invention is the use of an "interpretation means", such as interpreter 72, which will "read" the test card 22, along with an encoder 76 that may be employed to generate (e.g. print) a result summary 82. The result summary 82 is contemplated to include one or more printed bar code indicia. In a preferred embodiment of the present invention, the result summary 82 may be provided (printed) using standard bar code symbologies (such as Code 39, Interleaved 2 of 5, PDF417, etc.), and accordingly could be read using "off-the-shelf" scanning devices and decoders to provide scanner 54a and decoder 54b of FIG. 3. An advantage of the arrangement of FIG. 4, is that the assaying means 32 need not be configured initially in a "standard" bar code indicia. For instance, rather than configuring the machine readable assaying means 32 in standard bar code language format, a customized configuration can be employed (by using, for instance, optical scan sheets). It is the function of the interpreter 72 and the encoder 76 to then decipher this customized configuration and provide a standard bar code indicia (that is scannable by low cost and known devices and apparatus).

The aforementioned configuration of the machine readable assaying system of the instant invention render said system capable of being employed on-site at an employer's individual location. A donor individual is given a collection container and provided a private environment where said donor individual is to excrete a specimen volume of urine into the collection container for analysis. A volume of urine is then brought into contact with the test card 22 (by bathing the test card 22 with a small amount of urine, inserting the test card 22 into the urine, etc.) The quality control indication means 38 and/or the control test strips 34 are then checked to assure the integrity of the assaying means 32. Assuming that the assay is functioning properly, the adulteration detection means 36 are then checked to determined whether the donor individual tampered with the specimen. If the adulteration detection means 36 indicate that the specimen is unadulterated, then the machine readable assaying means 32 are then read by the test card reading unit 54 (such as the scanner 54a and decoder 54b). The results of the assay are then stored in the memory unit 62B of the controller module 62 for transmission to a desired location such as the centralized laboratory 58.

Upon the central laboratory 58 receiving the assay data, the names or identification codes of those donor individuals who provided negative results may be immediately communicated to prospective employers, so that those particular donors may be offered employment. All positive assay urine specimens will be requested from the test site by the central laboratory 58 for further confirmation analysis. Accordingly, the employer is immediately provided with a number of qualified potential employees to choose from, and the privacy concerns of the donor individual are safeguarded.

What is claimed is:

1. An on-site machine readable assaying system for detecting the absence of proscribed substances in human physiological fluids such as urine, said fluids emanating from a donor individual, comprising:

a) a test card; and b) machine readable assaying means comprising at least one individual analysis strip imprinted upon the test card, each analysis strip consisting of reagents which are capable of analyzing, detecting and visually signaling the presence of proscribed substances within human physiological fluid, at least one fixed strip and at least one blank region also located upon the test card, organized in a pattern with the individual analysis strips to produce an encoded machine readable source of data, wherein the analysis strips, upon detecting a proscribed substance, will change from a first color to a second darker color, hence altering the initial pattern of fixed strips, blank regions and analysis strips, thus producing encoded data which is distinct from that data which was previously encoded therein.

2. The on-site machine readable assaying system of claim 1, wherein adulteration detection means which are capable of determining whether a particular specimen of physiological fluid such as urine has been tampered with are located upon the test card.

3. The on-site machine readable assaying system of claim 2, further comprising quality control indication means which are configured to generate a signal upon contact with physiological fluid, regardless of the presence of proscribed substances, to ensure that the analysis strips of the machine readable assaying means are functioning properly.

4. The on-site machine readable assaying system of claim 3, wherein the adulteration detection means and quality control indication means are configured within the pattern of analysis strips, fixed strips and blank regions which comprise the machine readable source of data.

5. The on-site machine readable assaying system of claim 4, wherein a machine readable pattern encoding test card production information is located upon the test card.

6. The on-site machine readable assaying system of claim 5, further comprising alignment aids located upon the test card for assisting in the alignment of the test card for reading by an appropriate device.

7. The on-site machine readable assaying system of claim 1, further comprising a) a test card reading unit for scanning and decoding the encoded machine readable data source on the test card;

b) a controller module comprising a processor and a memory unit, the processor capable of processing and the memory unit of storing the decoded machine readable source of data gathered by the test card reading unit; and c) a communication module and a communication link, the communication module capable of transmitting the decoded data processed by the processor and stored in the memory unit to a distinct location such as a central laboratory via the communication link.

8. The on-site machine readable assaying system of claim 2, further comprising a) a test card reading unit for scanning and decoding the encoded machine readable data source on the test card;

b) a controller module comprising a processor and a memory unit, the processor capable of processing and the memory unit of storing the decoded machine readable source of data gathered by the test card reading unit; and c) a communication module and a communication link, the communication module capable of transmitting the decoded data processed by the processor and stored in the memory unit to a distinct location such as a central laboratory via the communication link.

9. The on-site machine readable assaying system of claim 7, further comprising a user interface module, the user interface module having a keyboard for allowing an individual to input certain data which is transmitted by the communication module along with the decoded and processed information gathered by the test card reading unit.

10. The on-site machine readable assaying system of claim 8, further comprising a user interface module, the user interface module having a keyboard for allowing an individual to input certain data which is transmitted by the communication module along with the decoded and processed information gathered by the test card reading unit.

11. A method of utilizing the on-site machine readable assaying system of claim 7, comprising the steps of:

a) bringing the volume of physiological fluid which has emanated from the donor into contact with the machine readable assaying means located upon the test card;

b) allowing a fixed period of time to elapse; and c) placing the test card reading apparatus adjacent to the test card, in order to scan and decode the encoded machine readable data source contained thereon.

12. The method of claim 11, further comprising the step of:

a) transmitting the decoded data to a distinct location, by means of the communication link.

13. A machine readable assaying system comprising:

a) a test surface having machine readable bar-code indicia imprinted thereupon; and b) analysis means configured within said machine readable bar-code indicia, capable of detecting and optically signaling the presence of a desired state, wherein the analysis means, upon detecting said state, cause the configuration of the machine readable bar-code indicia to change from a first configuration to a second configuration, thus producing encoded data in the second configuration which is distinct from that data which was previously encoded in the first configuration.

* * * * *